(12) United States Patent
Nakajima et al.

(10) Patent No.: US 6,599,748 B1
(45) Date of Patent: Jul. 29, 2003

(54) HARDNESS INDICATOR COMPOSITION AND METHOD OF WATER HARDNESS ANALYSIS

(75) Inventors: Junichi Nakajima, Hojo (JP); Keita Mizogami, Matsuyama (JP); Yuuji Ukena, Matsuyama (JP)

(73) Assignees: Miura Co., Ltd., Matsuyama (JP); Miura Institute of Research & Development Co. Ltd., Matsuyama (JP)

(*) Notice: Subject to any disclaimer, the term of this patent is extended or adjusted under 35 U.S.C. 154(b) by 91 days.

(21) Appl. No.: 09/716,434

(22) Filed: Nov. 21, 2000

(30) Foreign Application Priority Data

Nov. 25, 1999 (JP) .......................... 11-333568

(51) Int. Cl.⁷ .............................. G01N 33/18
(52) U.S. Cl. .................. 436/39; 534/839; 534/861; 534/871; 534/888; 534/884; 534/840; 534/841; 534/842
(58) Field of Search ................. 436/39; 534/839, 534/861, 874, 888, 884, 840–842, 871

(56) References Cited

U.S. PATENT DOCUMENTS

| 3,697,224 A | | 10/1972 | Means et al. | |
| 3,798,000 A | | 3/1974 | Helger | |
| 3,895,913 A | | 7/1975 | Bockowski et al. | |
| 3,934,977 A | * | 1/1976 | Cleaver | 436/74 |
| 4,205,953 A | * | 6/1980 | Miller | 422/62 |
| 4,205,955 A | | 6/1980 | Sloat | |
| 4,383,043 A | | 5/1983 | Denney et al. | |
| 4,454,230 A | * | 6/1984 | Denney | 422/61 |
| 4,503,156 A | * | 3/1985 | Yamazato et al. | 436/74 |
| 4,818,691 A | * | 4/1989 | Artiss et al. | 435/15 |
| 5,326,494 A | * | 7/1994 | Woods | 252/186.27 |
| 5,397,710 A | * | 3/1995 | Steinman | 422/56 |
| 5,482,866 A | * | 1/1996 | Denton et al. | 422/61 |
| 5,550,031 A | * | 8/1996 | Miyakawa et al. | 435/29 |
| 6,171,866 B1 | * | 1/2001 | He et al. | 436/79 |

OTHER PUBLICATIONS

Fundamentals of Analytical Chemistry, 6th Edition, Edited by Skoog, West and Holler, 1992, Chapter 13, pp. 286–308 and inside cover Acid Base Indicators Table.*
Quantitative Chemical Analysis, 4th Edition, Edited by Harris, 1995, Chapter 13–5, pp. 328–336.*

* cited by examiner

Primary Examiner—Mark L. Bell
Assistant Examiner—Jennine Brown
(74) Attorney, Agent, or Firm—Birch, Stewart, Kolasch & Birch, LLP

(57) ABSTRACT

A hardness indicator composition, and a method of water hardness analysis, capable of measuring hardness even with higher-hardness water without requiring titration by a two-liquid system. The hardness indicator composition is formulated of a metal indicator with a desensitizer added thereto.

4 Claims, 2 Drawing Sheets

F I G. 1
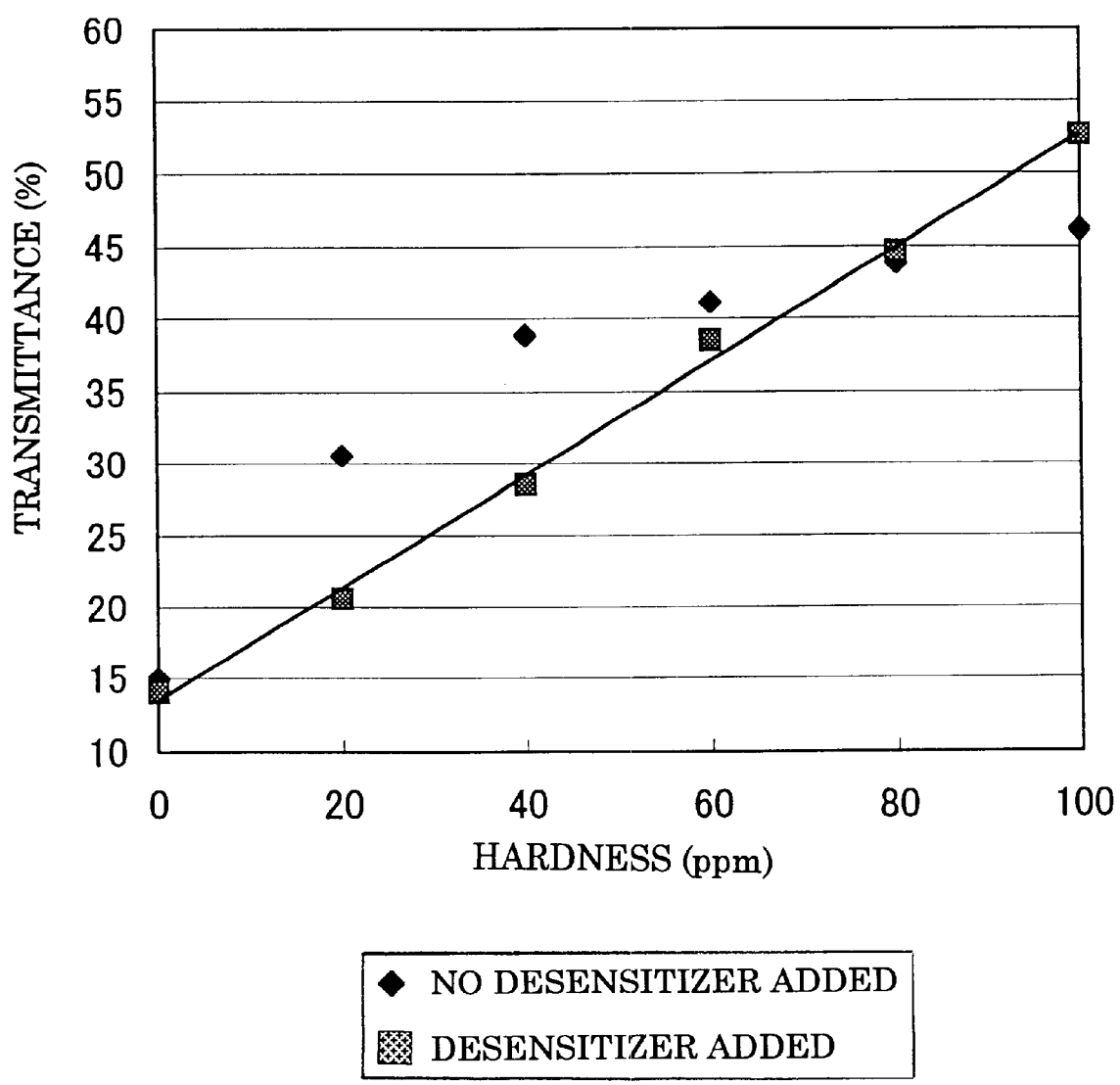

HARDNESS INDICATOR COMPOSITION AND METHOD OF WATER HARDNESS ANALYSIS

BACKGROUND OF THE INVENTION

The present invention relates to a hardness indicator composition for measuring the hardness of industrial water, daily life water and the like as well as a method of water hardness analysis using the hardness indicator.

As is well known, on feed water lines leading to cooling and hotting systems such as boilers, water heaters and cooling towers, devices for removing hardness contained in the feed water are used from the need for preventing scale deposition within the cooling and hotting systems. Among others, automatic regenerative water softeners (hereinafter, referred to as water softener) of the type that hardnesses are removed by using ion exchange resins have been widely used.

Conventionally, as the hardness measurement of the raw of the water softener (generally, high in hardness), there has been available a method of determining the hardness by titration with EDTA (ethylenediamine tetraacetate) by using a metal indicator (Calmagite, EBT (Eriochrome Black T), or the like) which changes in color through reaction with hardness (Ca, Mg, etc.) in an alkaline condition. This method, however, involves titration with a two-liquid system, thus taking much time and labor for measurement. For this reason, there has been a desire for implementation the hardness measurement with a one-liquid system without involving titration with EDTA.

Conventional indicators for use of detection of hardness leakage are effective for detecting hardnesses in the treated water of the water softener. However, those indicators, because of their too narrow range of measurement, cannot be used for the hardness measurement of raw water of the water softener. For this reason, there has been a desire for indicators capable of measuring even high-hardness feed water.

SUMMARY OF THE INVENTION

In view of these and other problems, an object of the present invention is to provide a hardness indicator composition, as well as a method of water hardness analysis, which makes it possible to measure the hardness without requiring titration with a two-liquid system and yet to measure the hardness of even high-hardness feed water.

The present invention having been achieved with a view to solving the above problems, according to a first aspect of the invention, there is provided a hardness indicator composition which is formulated of a metal indicator with a desensitizer added thereto.

In one aspect of the invention, the metal indicator contains a dye represented by any one of General formulas (I)–(III):

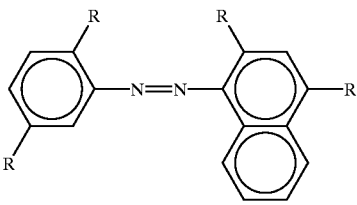

General formula (I)

wherein R is any one of H, OH, $NO_2$, $CH_3$, $SO_3H$ and COOH,

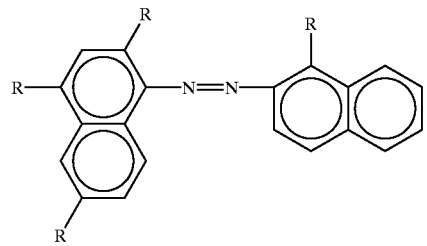

General formula (II)

where R is any one of H, OH, $NO_2$, $CH_3$, $SO_3H$ and COOH, and

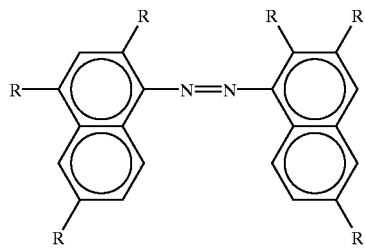

General formula (III)

where R is any one of H, OH, $NO_2$, $CH_3$, $SO_3H$ and COOH.

In an embodiment of the invention, the desensitizer is an organic polybasic acid, or a salt thereof, having two or more carboxyl groups.

And, according to the present invention, there is provided a method of water hardness analysis using an indicator as defined in any one of the aspects of the invention, the method comprising the steps of adding the indicator to a sample solution, and then determining a change in color of the sample solution according to an optical transmittance in a vicinity of a specific wavelength.

Further, according to the present invention, there is provided a method of water hardness analysis using an indicator as defined in any one of the aspects of the invention, the method comprising the steps of adding the indicator to a sample solution, and then determining a change in color of the sample solution according to an optical transmittance in vicinities of two or more specific wavelengths.

BRIEF DESCRIPTION OF THE DRAWINGS

FIG. 1 is a graph showing results of measuring the relationship between the transmittance of Calmagite and the hardness at a wavelength of 610 nm.

DETAILED DESCRIPTION OF THE PREFERRED EMBODIMENTS

Figure 2:
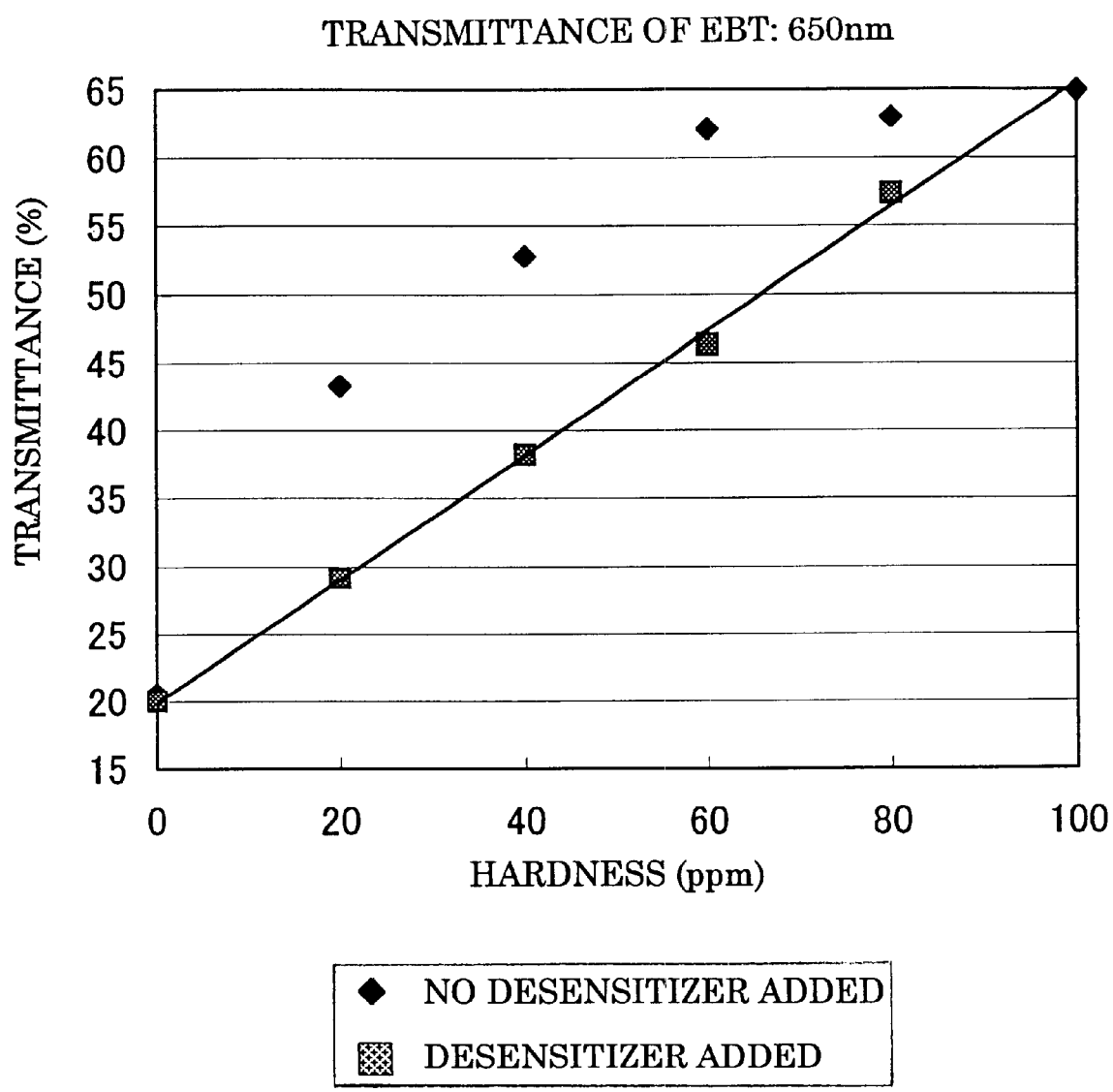
FIG. 2 is a graph showing results of measuring the relationship between the transmittance of EBT and the hardness at a wavelength of 650 nm.

Next, embodiments of the invention are described. The present invention can suitably be embodied to measure the hardness of a sample solution, such as raw water of the water softener in a feed water line leading to a boiler. As a main component of a hardness indicator composition according to the present invention, a metal indicator is applied. An advantage of using a metal indicator is that the metal indicator is a kind of chelating reagent, which generates complex ions in combination with metal ions, such as magnesium ions or calcium ions, those which are main components of the hardness, thus the metal indicator developing color even more sensitively and being suitable for hardness measurement. Applicable as the metal indicator in the invention are Calmagite, EBT, NN indicator and the like.

The desensitizer (which is a chemical that forms complex ions in combination with part of metal ions of the hardness in the water to reduce the metal ions that react with the metal indicator) needs to be one which exhibits reactions similar to those of metal indicators but which has such a reactivity that the desensitizer does not form complex ions with all metal ions. By using the desensitizer, measurements can be achieved in the same fashion as with low-hardness measurements. That is, even with a sample solution of high hardness, a high accuracy measurement becomes achievable. As the desensitizer for the hardness indicator composition of this invention, polyacrylates, iminodiacetates, citrates and the like are applicable.

As to the method of water hardness analysis, a specified amount of the sample solution is introduced into a transparent container, a quantitated amount of the indicator is injected into the transparent container, and the hue of the sample solution in the vicinity of specific wavelengths is determined by a detection means.

As shown above, with the method of water hardness analysis according to the invention, the hardness of a sample solution can be measured without using EDTA and with a one-liquid system.

EXAMPLES

Next, a concrete example of the present invention is described in detail. As a main component of the hardness indicator composition according to the invention, first of all, the metal indicator is explained. For the selection of the metal indicator, it is important for the metal indicator to develop color against hardness. A further condition for the selection of the metal indicator is that a local maximum of absorption exists at specific absorption wavelengths in the color of the metal indicator. It is still also important for the metal indicator to have a certain level of solubility and be free from performance deterioration when formed into an aqueous solution. Consequently, Calmagite or the like represented by general formula (I) is suitable as the metal indicator that satisfies the foregoing conditions:

General formula (I)

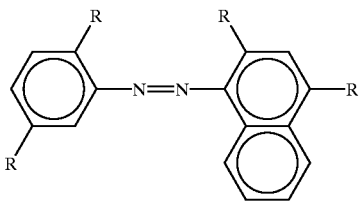

where R is any one of H, OH, NO$_2$, CH$_3$, SO$_3$H and COOH.

Also, EBT, Eriochrome Blue Black B or the like represented by General formula (II) is suitable as the metal indicator:

General formula (II)

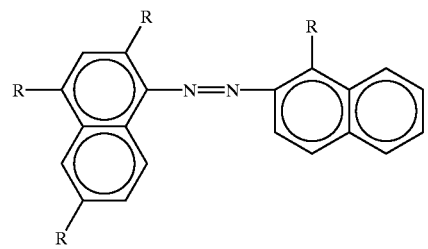

where R is any one of H, OH, NO$_2$, CH$_3$, SO$_3$H and COOH.

Further, NN indicator, hydroxynaphthol blue, chalcone or the like represented by General formula (III) is suitable as the metal indicator:

General formula (III)

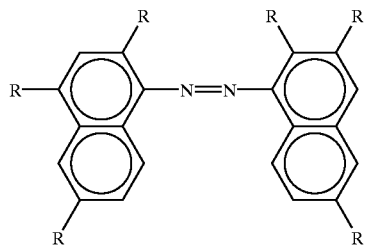

where R is any one of H, OH, NO$_2$, CH$_3$, SO$_3$H and COOH.

Now, Calmagite as a concrete example of the metal indicator is explained. Calmagite forms complex ions in combination with magnesium ions, calcium ions, zinc ions, lead ions and cadmium ions, changing from blue to red to serve for metal detection.

In this connection, taking into consideration that measurements are difficult for the metal indicator to achieve with high hardnesses, we inventors energetically repeated researches and experiments and, as a result, found that adding a desensitizer to the metal indicator makes it possible to achieve the measurement with a one-liquid system.

Therefore, the desensitizer to be added to the metal indicator is explained. The desensitizer in this case exhibits a chelate effect similar to that of the metal indicator. However, the desensitizer differs from the metal indicator in that the metal indicator forms complex ions in combination with all hardness-component metal ions, while the desensitizer forms complex ions in combination with part of the hardness-component metal ions. For this reason, metal ions in the sample solution decrease, thereby allowing the resulting measurement to be similar to measurements with low-hardness sample solutions and thus making it possible to achieve measurements of high-hardness sample solutions. For selection of the desensitizer that satisfies these conditions, Table 1 shows judgment results as to whether the desensitizers are effective for the present invention in terms of "Ca chelate stability constant" and "solubility." The "Ca chelate stability constant" refers to the chelating power with calcium, and the "solubility" refers to the weight of the desensitizer soluble in 100 g of water. Symbol " " in results represents usableness as the desensitizer, and "×" represents unusableness as the desensitizer.

TABLE 1

| Desensitizer | Ca chelate stability constant, logK | Solubility, g/100 g water | Result |
| --- | --- | --- | --- |
| Na polyacrylate | <2.0 | over 40 |  |
| K polyacrylate | <2.0 | over 40 |  |
| 2Na iminodiacetate | 2.59 | 10 |  |
| 2K iminodiacetate | 2.59 | — |  |
| 2Na citrate | <2.0 | over 10 |  |
| 2K citrate | <2.0 | over 10 |  |
| 3Na nitrilotriacetate | 6.41 | 2.0 | x |
| EDTA-2Na | 10.96 | 11.1 | x |
| EDTA-2K | 10.96 | 100 | x |

Referring to Table 1, since increasing "Ca chelate stability constant" causes increasing amount of chelate formed, the "Ca chelate stability constant", unless it is at a certain low level, does not satisfy the conditions and therefore is unusable. Also, desensitizers having low "solubilities" are hard to solve in water, thus difficult to use. This requires the desensitizer to have a solubility of a certain high level. Consequently, desensitizers satisfying these conditions (sodium polyacrylate, sodium iminodiacetate, sodium citrate, etc.) are effectively operative as the desensitizer of the present invention. Accordingly, Table 1 show the results of judgment determined by taking into account these conditions.

In more detail for the description of the present invention, the inventors performed experiments by using a 99.5 wt % organic solvent with a 0.5 wt % metal indicator (Calmagite) added thereto, and by an 89.5 wt % organic solvent with a 0.5 wt % metal indicator (Calmagite) and a 10 wt % desensitizer (sodium polyacrylate) added thereto. As the organic solvent in this case, ethylene glycol and triethanolamine were used.

First, results obtained when Calmagite was used as the metal indicator and sodium polyacrylate was used as the desensitizer are shown in FIG. 1. The wavelength of 610 nm used in this case represents the maximum absorption wavelength of Calmagite. As apparent from FIG. 1, the addition of the desensitizer develops an almost linear relationship between hardness and transmittance, allowing concentration determination for hardness to be easily achieved, whereas use of the metal indicator alone results in a nonlinear relationship, making it hard to make concentration determination for hardness. Thus, effects of adding the desensitizer can be seen apparently.

In this connection, the inventors performed experiments also with the above-mentioned EBT by the same method as with Calmagite. Results of this, as shown in FIG. 2, were confirmed nearly the same as with Calmagite. In this case, because the maximum wavelength of EBT is 650 nm, the experiments were performed at a wavelength of 650 nm.

The inventors further performed experiments also with other metal indicators such as the above-mentioned NN indicator by the same method as with Calmagite and EBT. Results of this as well were confirmed nearly the same as with Calmagite and EBT.

Next, the method of water hardness analysis using the hardness indicator composition is explained. First, a specified amount of raw water of a water softener (not shown), i.e., a sample solution is introduced into a transparent container (not shown). Then, with a quantitative dispenser such as roller pump (not shown), the indicator according to the present invention is injected in doses, thereby mixed, into the transparent container. Then, light emitted from a light source (not shown) through the transparent container is received by a light receiver (not shown), and changes in hue of the subject solution are measured based on the strength of light received by the light receiver. By this measurement, concentration determination for hardness of the sample solution is performed. Consequently, the method of water hardness analysis in the present invention is based on the use of calorimetric analysis.

In this case, because the above-mentioned metal indicators have their individual unique maximum absorption wavelengths, measurement wavelength differs depending on the components of the indicator. As a concrete example, a case using Calmagite as the metal indicator is explained. As described above, the maximum wavelength of Calmagite is 610 nm. An advantage of measuring with the maximum wavelength is that accurate measurements can be obtained over the widest possible range. Widening the measurable range for hardness in turn makes it possible to measure water the concentration of hardness of which is unknown.

Further, as the human eyes are capable of discerning changes in hue of Calmagite with different hardnesses (red to blue colors) by the visual sense, hardness determination can be achieved by preparing color samples of these hues and making comparisons with these color samples. For machine automatization of this work, analyzing two or three or more wavelength without limiting to one wavelength for measurement allows the same results as in the evaluation with the human eyes to be obtained.

As described hereinabove, according to the present invention, there can be provided a hardness indicator composition for hardness measurement of raw water, as well as a method of water hardness analysis using this indicator, which allow measurement with a one-liquid system to be achieved. Once high-hardness measurement has become implementable, total flow volume up to the exhaustion point can be accurately determined from the exchangeability of the water softener (exchangeability of ion exchange resins used in the water softener), so that the timing for regeneration can be accurately determined.

What is claimed is:

1. A hardness indicator composition comprising a metal indicator which contains a dye represented by any one of general formulas (I)–(III):

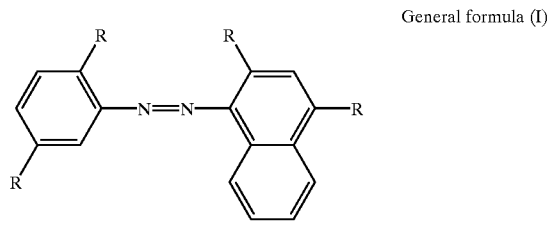

General formula (I)

wherein R is any one H, OH, NO$_2$, CH$_3$, SO$_3$H and COOH,

General formula (II)

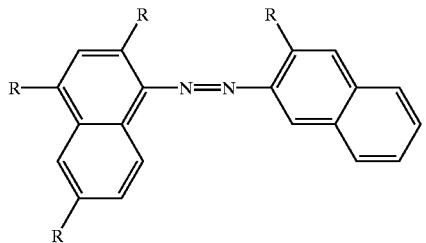

where R is any one of H, OH, NO$_2$, CH$_3$, SO$_3$H and COOH, and

General formula (III)

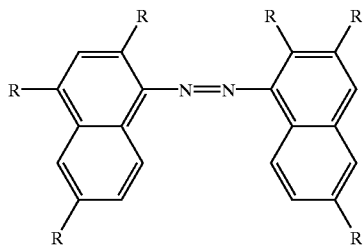

where R is any one of H, OH, NO$_2$, CH$_3$, SO$_3$H and COOH, and a desensitizer, wherein the desensitizer has a Ca chelate stability constant ≦2.59.

2. The hardness indicator composition according to claim 1, wherein the desensitizer is an organic polybasic acid, or a salt thereof, having two or more carboxyl groups.

3. A method of water hardness analysis using an indicator as defined in claim 1, comprising the steps of adding the indicator to a sample solution, and then determining a change in color of the sample solution according to an optical transmittance in a vicinity of a specific wavelength.

4. A method of water hardness analysis using an indicator as defined in claim 1, comprising the steps of adding the indicator to a sample solution, and then determining a change in color of the sample solution according to an optical transmittance in vicinities of two or more specific wavelengths.

* * * * *